(12) United States Patent
Masuda et al.

(10) Patent No.: US 8,858,499 B2
(45) Date of Patent: *Oct. 14, 2014

(54) LIQUID INJECTOR FOR INJECTING CONTRAST MEDIUM AT VARIABLE RATE INTO A SUBJECT WHO IS TO BE IMAGED BY IMAGING DIAGNOSTIC APPARATUS

(71) Applicants: Nemoto Kyorindo Co., Ltd., Tokyo (JP); Atsushi Hatcho, Nagano (JP)

(72) Inventors: Kazumasa Masuda, Tokyo (JP); Atsushi Hatcho, Nagano (JP)

(73) Assignees: Nemoto Kyorindo Co., Ltd., Tokyo (JP); Atsushi Hatcho, Nagano (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/925,266

(22) Filed: Jun. 24, 2013

(65) Prior Publication Data

US 2013/0281849 A1    Oct. 24, 2013

Related U.S. Application Data

(63) Continuation of application No. 10/657,440, filed on Sep. 8, 2003, now Pat. No. 8,486,017.

(30) Foreign Application Priority Data

Sep. 26, 2002 (JP) ................................. 2002-281109

(51) Int. Cl.
| | |
|---|---|
| *A61M 37/00* | (2006.01) |
| *A61M 31/00* | (2006.01) |
| *A61M 5/00* | (2006.01) |
| *A61M 5/145* | (2006.01) |
| *A61M 5/172* | (2006.01) |
| *G05D 7/06* | (2006.01) |
| *A61M 5/142* | (2006.01) |

(52) U.S. Cl.
CPC ............. *A61M 5/007* (2013.01); *A61M 31/005* (2013.01); *A61M 2005/14208* (2013.01); *A61M 5/1456* (2013.01); *A61M 5/172* (2013.01); *G05D 7/0617* (2013.01)
USPC ........................................................ 604/131

(58) Field of Classification Search
USPC .................................... 604/131; 128/DIG. 13
See application file for complete search history.

(56) References Cited

U.S. PATENT DOCUMENTS

| | | | |
|---|---|---|---|
| 4,006,736 A | 2/1977 | Kranys et al. | |
| 5,408,847 A | 4/1995 | Erickson | |

(Continued)

FOREIGN PATENT DOCUMENTS

| | | |
|---|---|---|
| EP | 0 576 740 A1 | 1/1994 |
| JP | 2000-506398 A | 5/2000 |

(Continued)

OTHER PUBLICATIONS

Office Action issued by the Japanese Patent Office on Jun. 29, 2010 for the counterpart Japanese Patent Application No. 2002-281109.

(Continued)

*Primary Examiner* — Kevin C Sirmons
*Assistant Examiner* — Deanna K Hall
(74) *Attorney, Agent, or Firm* — Knobbe Martens Olson & Bear LLP

(57) ABSTRACT

A liquid injector registers the data of a variable pattern in which an injection rate of a contrast medium varies with time. The injection rate of the contrast medium varies with time according to the variable pattern for maintaining a state in which the image contrast achieved by the contrast medium approximates an optimum level.

15 Claims, 9 Drawing Sheets

(56) References Cited

U.S. PATENT DOCUMENTS

| | | |
|---|---|---|
| 5,450,847 A | 9/1995 | Kampfe et al. |
| 5,592,940 A | 1/1997 | Kampfe |
| 5,681,286 A | 10/1997 | Niehoff |
| 5,840,026 A * | 11/1998 | Uber et al. .................... 600/431 |
| 6,055,985 A | 5/2000 | Bae et al. |
| 8,486,017 B2 * | 7/2013 | Masuda et al. ................ 604/131 |

FOREIGN PATENT DOCUMENTS

| | | |
|---|---|---|
| JP | 2000-189515 A | 7/2000 |
| JP | 2002-11096 | 1/2002 |
| JP | 2002-102343 | 4/2002 |
| WO | WO 97/12550 | 4/1997 |
| WO | WO 97/21456 | 6/1997 |
| WO | WO 00/61025 | 10/2000 |
| WO | WO 01/07442 A1 | 10/2001 |

OTHER PUBLICATIONS

Jun Hatcho et al., 172 "The collection of drafts" of "The 58th general meeting scientific convention" by "Japanese Society of Radiological Technology" on Apr. 4-7, 2002, p. 149.

* cited by examiner

LIQUID INJECTOR FOR INJECTING CONTRAST MEDIUM AT VARIABLE RATE INTO A SUBJECT WHO IS TO BE IMAGED BY IMAGING DIAGNOSTIC APPARATUS

RELATED APPLICATIONS

This application is a continuation of U.S. patent application Ser. No. 10/657,440, filed Sep. 8, 2003, which claims priority to Japanese Patent Application No. 2002-281109, filed Sep. 26, 2002, the content of which is incorporated herein it its entirety.

BACKGROUND OF THE INVENTION

1. Field of the Invention

The present invention relates to a liquid injector for injecting a liquid into a subject, and more particularly to a liquid injector for injecting a liquid into a subject who is to be imaged by an imaging diagnostic apparatus such as a CT (Computed Tomography) apparatus, an MRI (Magnetic Resonance Imaging) apparatus, an angiography apparatus, or the like.

2. Description of the Related Art

Presently available imaging diagnostic apparatus for capturing fluoroscopic images of subjects include CT scanners, MRI apparatus, PET (Positron Emission Tomography) apparatus, ultrasonic diagnostic apparatus, CT angiography apparatus, MR angiography apparatus, and ultrasonograph.

When such an imaging diagnostic apparatus is used to capture a fluoroscopic image of a subject, it is occasionally practiced to inject a liquid such as a contrast medium or a saline solution into the subject. There have been liquid injectors in practical use for automatically injecting a liquid into a subject (see, for example, patent documents 1, 2 below).

Patent document 1: Japanese laid-open patent publication No. 2002-11096;

Patent document 2: Japanese laid-open patent publication No. 2002-102343.

Such a liquid injector has a liquid injection mechanism comprising a drive motor and a slider mechanism, and employs a liquid syringe that is removably mounted on the liquid injection mechanism. The liquid syringe comprises a cylinder and a piston slidably inserted in the cylinder. The cylinder is filled with a liquid, e.g., a contrast medium, to be injected into the subject.

The liquid syringe is connected to the subject by an extension tube and set on the liquid injection mechanism. The liquid injection mechanism individually holds the piston and the cylinder and moves them relatively to each other for injecting a liquid, typically a contrast medium, from the liquid syringe into the subject. If the operator of the liquid injector enters the data of an injection rate for the contrast medium into the liquid injector, then the liquid injector injects the contrast medium into the subject at the injector rate whose data have been entered into the liquid injector. The injected contrast medium changes the image contrast of the subject, allowing the imaging diagnostic apparatus to capture a good fluoroscopic image of the subject.

Thus, the liquid injector can inject a contrast medium into a subject to be imaged by an imaging diagnostic apparatus in order to change the image contrast of the subject so that the imaging diagnostic apparatus is able to capture a good fluoroscopic image of the subject.

There has been conducted an experiment in which a contrast medium for CT was actually injected into a subject by a liquid injector and a CT value representing an image contrast was measured. The results of the experiment have indicated that, as shown in FIG. 11 of the accompanying drawings, the CT value increased nonlinearly and then quickly decreased, and remained at an optimum level only for a short period of time. Therefore, even when a contrast medium is injected into a subject using the conventional liquid injector, it is difficult for the imaging diagnostic apparatus to capture a good fluoroscopic image of the subject.

Moreover, as shown in FIG. 11, the CT value has its peak level much higher than the optimum level, indicating that the subject is dosed with an excessive amount of contrast medium. Consequently, the contrast medium is consumed too much, and tends to adversely affect the subject's health. Simply reducing the amount of contract medium to be injected into the subject would not solve the problem because the period of time in which the CT value approximates the optimum level would be reduced, making it more difficult to capture a good fluoroscopic image of the subject.

SUMMARY OF THE INVENTION

It is therefore an object of the present invention to provide a liquid injector which is capable of injecting a contrast medium into a subject in order to maintain a state in which the image contrast produced by the injected contrast medium approximates an optimum level.

A liquid injector according to the present invention has a liquid injection mechanism, a pattern storing means, and a rate controlling means. The liquid injection mechanism injects a contrast medium into a subject whose fluoroscopic image is to be captured by an imaging diagnostic apparatus. The pattern storing means registers data of a variable pattern in which an injection rate of the contrast medium varies with time. The rate controlling means varies an operating speed of said liquid injection mechanism with time according to said variable pattern. Since the injection rate of the contrast medium varies with time according to the variable pattern, a state in which the image contrast achieved by the contrast medium approximates an optimum level is maintained. Therefore, an optimum fluoroscopic image of the subject can be captured. The contrast medium is consumed in a minimum amount that is required, and hence the subject is prevented from being dosed with an unduly excessive amount of contrast medium.

The various means referred to in the present invention may be arranged to perform their stated functions, and may be implemented by dedicated pieces of hardware for performing the functions, data processing apparatus for performing the functions according to computer programs, functions achieved in data processing apparatus according to computer programs, or combinations thereof.

The various means referred to in the present invention are not required to be individually independent entities, and may be arranged such that a plurality of means may be constructed as a single apparatus, a certain means may be part of another means, or part of a certain means and part of another means overlap each other.

A computer unit referred to in the present invention may comprise a piece of hardware capable of reading the data of a computer program and performing a processing operation according to the computer program, and may comprise a CPU (Central Processing Unit) to which are connected various devices including a ROM (Read Only Memory), a RAM (Random Access Memory), an I/F (Interface) unit, etc.

According to the present invention, enabling a computer unit to carry out various operations according to a computer program also signifies enabling the computer unit to control operation of various devices to carry out various operations. For example, storing various data in a computer unit may signify enabling a CPU to store various data in an information storage medium such as a RAM or the like fixedly mounted in the computer unit, or enabling a CPU to store various data in an information storage medium such as an FD (Flexible Disc-cartridge) or the like replaceably loaded in the computer unit through an FDD (FD Drive).

An information storage medium referred to in the present invention may comprise a piece of hardware which stores in advance a computer program for enabling a computer unit to perform various processing operations. An information storage medium may comprise, for example, a ROM or an HDD (Hard Disc Drive) fixedly mounted in the computer unit, or a CD (Compact Disc)-ROM or an FD replaceably loaded in the computer unit.

The above and other objects, features, and advantages of the present invention will become apparent from the following description with reference to the accompanying drawings which illustrate examples of the present invention.

DETAILED DESCRIPTION OF THE PREFERRED EMBODIMENTS

Figure 2:
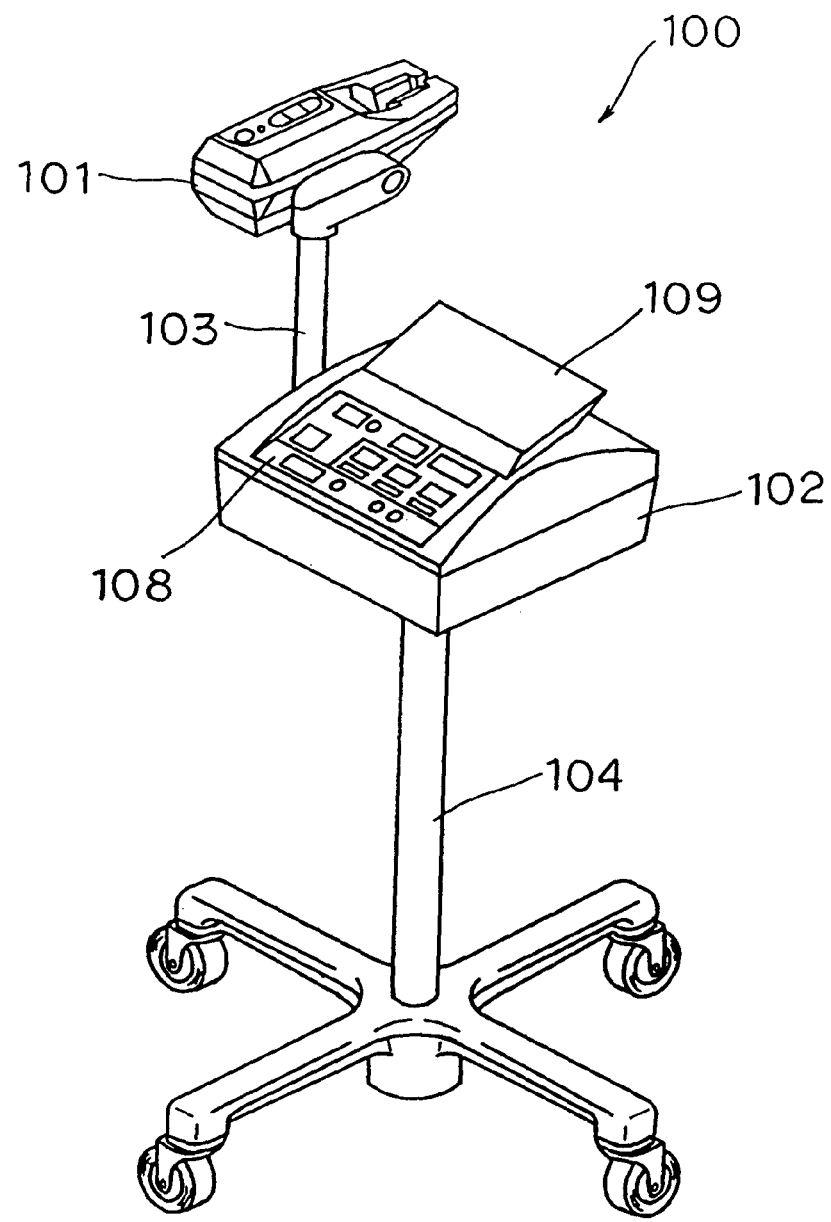
FIG. 2 is a perspective view of the liquid injector.

Arrangement of the Liquid Injector:

As shown in FIG. 2, liquid injector 100 according to an embodiment of the present invention comprises injection head 101 and main body 102. Main body 102 is mounted on the upper end of stand 103. Arm 104 is vertically mounted on a side wall of main body 102, and injection head 110 is mounted on the upper end of arm 104.

Figure 3:
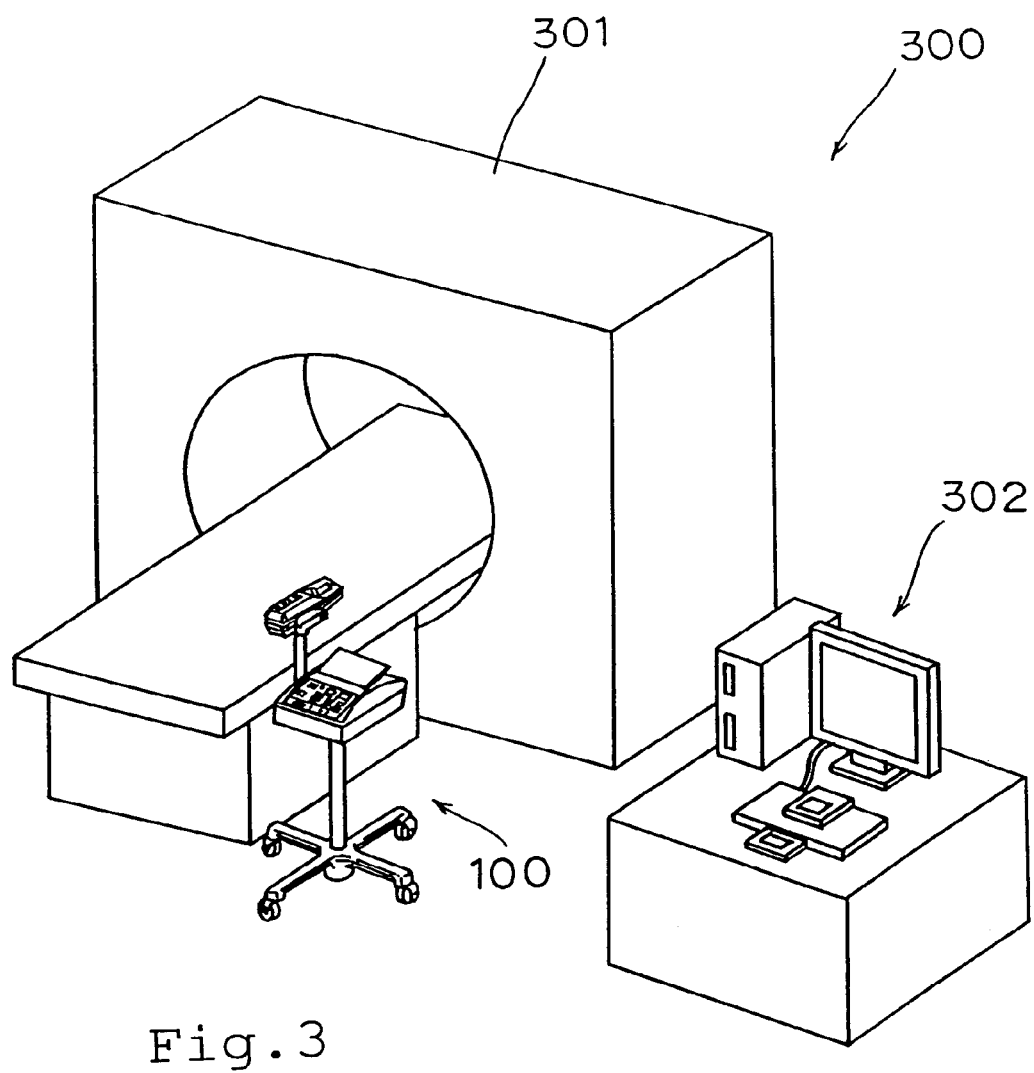
FIG. 3 is a perspective view of a CT scanner as an imaging diagnostic apparatus.

As shown in FIG. 3, liquid injector 100 is used near imaging unit 301 of CT scanner 300 which serves as an imaging diagnostic apparatus. Liquid injector 100 injects a contrast medium as a liquid from liquid syringe 200 into a subject (not shown) who is to be imaged by CT scanner 300.

Figure 4:
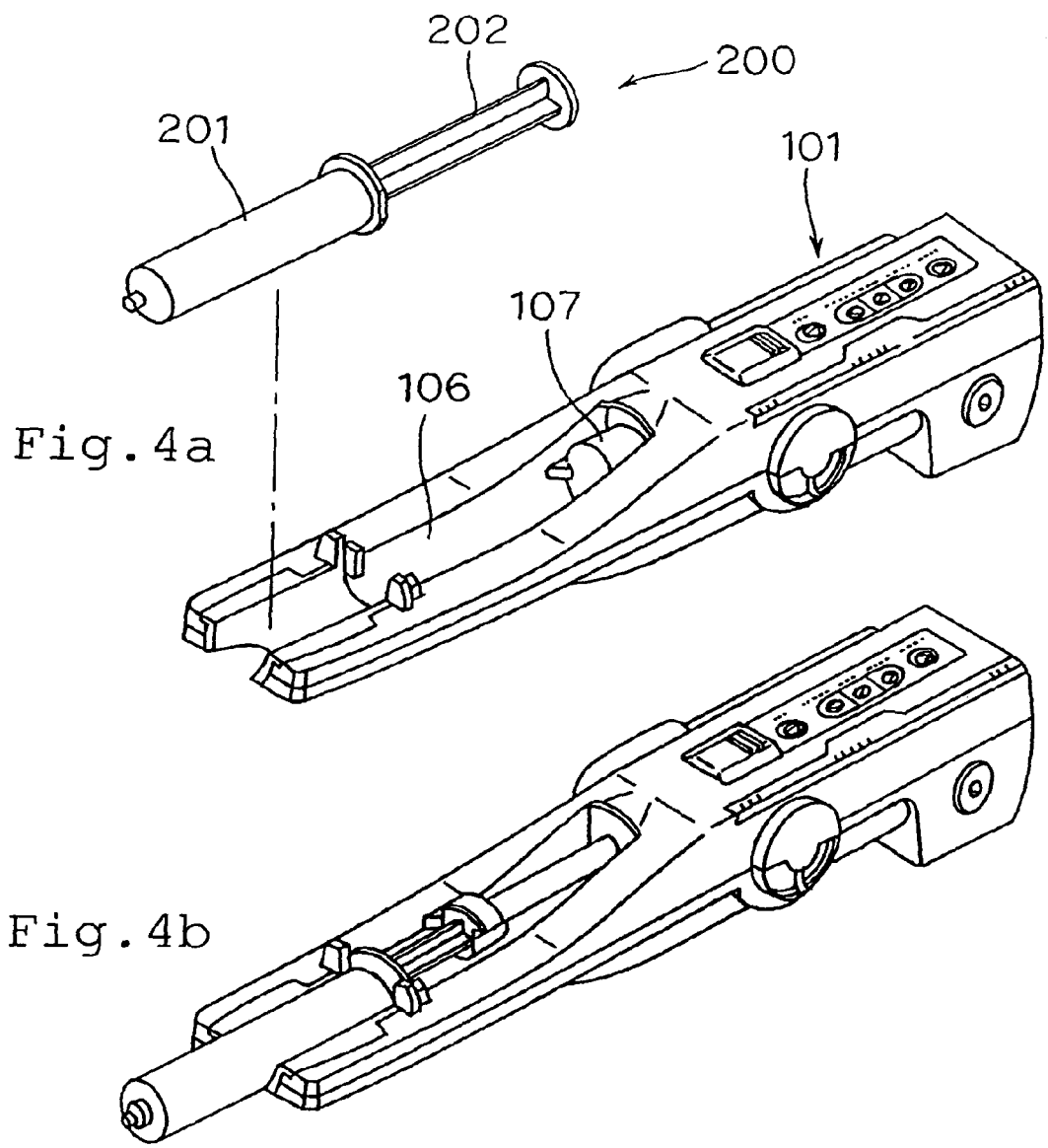
FIGS. 4a and 4b are perspective view showing the manner in which a liquid syringe is set on an injection head of the liquid injector.

As shown in FIG. 4, liquid syringe 200 comprises cylinder 201 and piston 202 slidably inserted in cylinder 201. Injection head 101 of liquid injector 100 holds cylinder 201 of syringe 200, which is replaceable, in recess 106 that is defined in an upper surface of injection head 101. Injection head 101 has syringe actuating mechanism 107 as liquid injection mechanism disposed behind recess 106. Syringe actuating mechanism 107 grips piston 202 of syringe 200 that is held in recess 106 and slides piston 202 into and out of cylinder 201.

Figure 5:
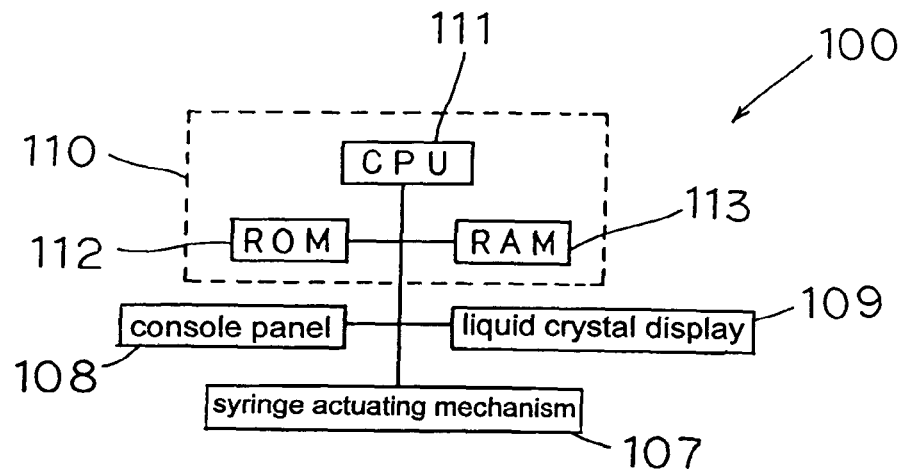
FIG. 5 is a block diagram of an electric circuit arrangement of the liquid injector.

As shown in FIG. 2, main body 102 has console panel 108 and liquid crystal display panel 109. As shown in FIG. 5, console panel 108, liquid crystal display panel 109, and syringe actuating mechanism 107 are connected to computer unit 110. Computer unit 110 comprises CUP 111, ROM 112, and RAM 113. A computer program and resources for CPU 111 are stored as software in at least one of ROM 112 and RAM 113.

Figure 1:
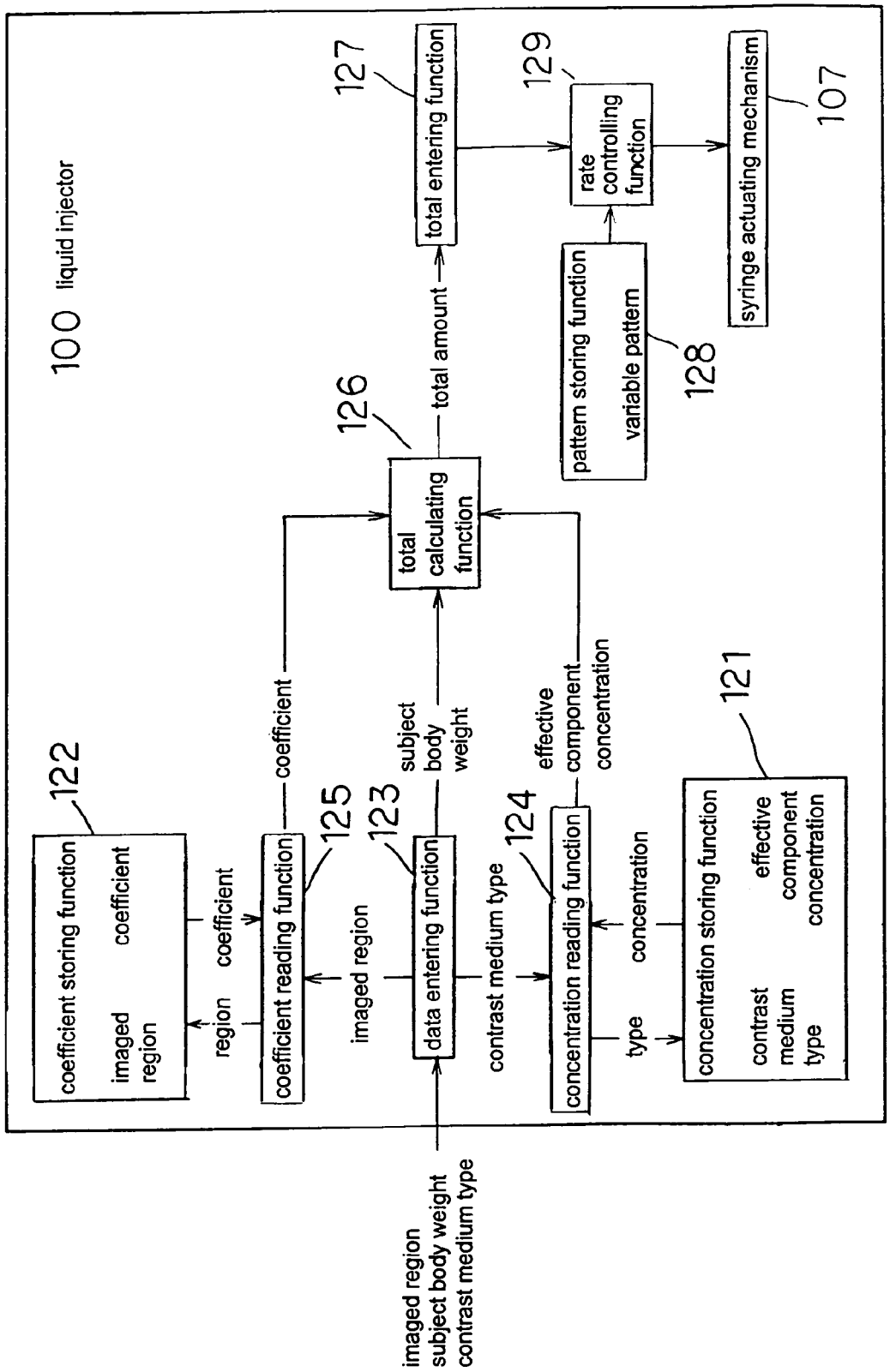
FIG. 1 is a block diagram showing a logic structure of a liquid injector according to an embodiment of the present invention.

When the CPU 111 reads the software from one of ROM 112 and RAM 113 and performs various processing sequences based on the software, liquid injector 100 logically has, as various means, various functions including, as shown in FIG. 1, concentration storing function 121, coefficient storing function 122, data entering function 123, concentration reading function 124, coefficient reading function 125, total calculating function 126, total entering function 127, pattern storing function 128, and rate controlling function 129.

Concentration storing function 121 corresponds to a storage area that is constructed in ROM 112 for CPU 111 to recognize data stored therein according to the computer program. Concentration storing function 121 stores the data of concentrations of an effective component contained in respective different types of contrast mediums. More specifically, since there are available a plurality of different types of contrast mediums for CT which contain different concentrations of iodine as an effective component, ROM 112 stores the data of concentrations of iodine contained in the respective different types of contrast mediums.

Coefficient storing function 122 also corresponds to a storage area in ROM 112 and stores the data of coefficients given to regions to be imaged of a subject. More specifically, since CT scanner 300 captures images of different regions, e.g., "head", "chest", etc. of a subject, ROM 112 stores the data of coefficients given to those regions to be imaged of the subject. These coefficients are used to calculate a total amount of contrast medium to be injected into the subject, as described later on, and are set to appropriate values that are established for the respective regions to be imaged based on experimental results.

Data entering function 123 is a function for CPU 111 to recognize the data of inputs that are entered into console panel 108, and enters the data of the body weight of a subject, regions to be imaged of the subject, and the type of a contrast medium used. The above functions correspond to functions for CPU 111 to perform predetermined processes according to the computer program. Concentration reading function 124 reads the data of the concentration of iodine based on the entered type of a contrast medium. Coefficient reading function 125 reads the data of coefficients corresponding to the regions to be imaged of a subject that have been entered.

Total calculating function 126 calculates a total amount of contrast medium to be injected into a subject in proportion to the body weight of the subject, in inverse proportion to the concentration of iodine contained in the contract medium used, and depending on the coefficients given to the regions to be imaged of the subject. Total entering function 127 enters the data of the total amount of contrast medium to be injected from total calculating function 126, and provides the entered data to rate controlling function 129.

More specifically, liquid injector 100 has registered therein total amounts of contrast medium to be injected into subjects based on the body weights of subjects, for example, as "A "(g/Kg)" based on experimental results. When the data of the body weight of a subject is entered as "B (Kg)", a total amount of iodine in proportion to the body weight is calculated as "A×B (g)".

Inasmuch as the data of concentrations of iodine contained in different types of contrast medium are registered as "C (g/ml)", when a type of contrast medium is entered, a total amount of the contrast medium to be injected is calculated as "(A×B)/C (ml)" in inverse proportion to the concentration. Furthermore, because the data of coefficients given to different imaging regions are registered as "D", when the data of a certain region to be imaged is entered, a total amount of contrast medium to be injected for the region to be imaged is calculated as "(A×B×D)/C (ml)".

Pattern storing function 128 corresponds to a storage area of ROM 112, and stores therein the data of a variable pattern according to which the injection rate of a contrast medium is to be varied with time. The data of a variable pattern is set to maintain a state in which a CT value serving as an image contrast approximates an optimum level.

Figure 6:
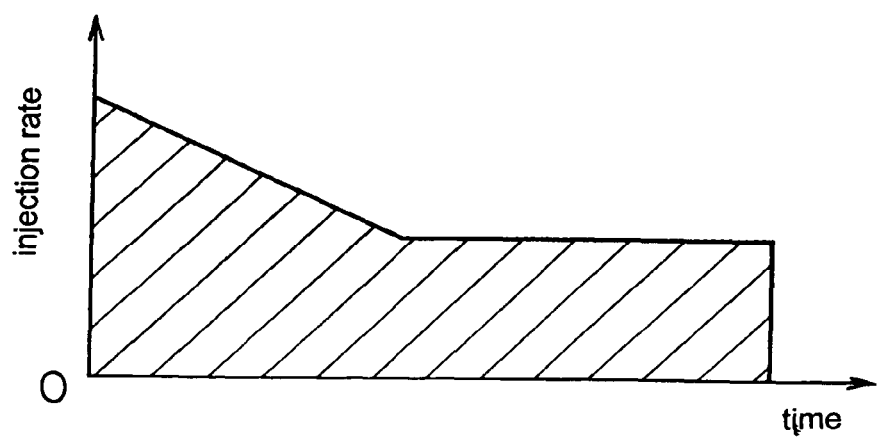
FIG. 6 is a diagram showing a variable pattern of an injection rate.

Rate controlling function 129 controls operation of syringe actuating mechanism 107 to inject a total amount of contrast medium that has been calculated by total calculating function 126 into a subject over a predetermined period of time. Rate controlling function 129 also varies, with time the injection rate of the contrast medium according to the variable pattern stored by pattern storing function 128. The variable pattern is set optimally based on experimental results, and is typically set such that, as shown in FIG. 6, the injection rate is linearly reduced for a certain period of time from the start of injection, and subsequently kept constant.

The above various functions of liquid injector 100 are accomplished by pieces of hardware such as console panel 108, they are mainly implemented by CPU 111 as a piece of hardware as it functions according to the resources and the computer program that are stored in an information storage medium such as ROM 112, etc.

The resources include registered data of total amounts of iodine to be injected based on the body weights of subjects, a data file of concentrations of iodine contained in different types of contrast mediums, a data file of coefficients assigned to regions to be imaged of subjects, registered data of a variable pattern, etc. The computer program is stored in an information storage medium such as RAM 113, etc. as software for enabling CPU 111 to perform various processing sequences to accept the entered data of the body weight of a subject, a region thereof to be imaged, and the type of a contrast medium from console panel 108, read the data of a concentration of iodine from ROM 112 based on the entered type of the contrast medium, read the data of a coefficient corresponding to the region to be imaged of the subject that has been entered, calculate a total amount of contrast medium to be injected into the subject in proportion to the body weight of the subject, in inverse proportion to the concentration of iodine contained in the contract medium used, and depending on the coefficient given to the region to be imaged of the subject, and control operation of syringe actuating mechanism 107 to inject the calculated total amount of contrast medium at an injection rate that varies with time according to the variable pattern for a predetermined period of time.

Operation of the Liquid Injector:

For using liquid injector 100 according to the present embodiment, the operator (not shown) connects liquid syringe 200 to the subject (not shown) placed in imaging unit 301 of CT scanner 300 with an extension tube. Cylinder 201 of liquid syringe 200 is held in recess 106 of injection head 101, and piston 202 is gripped by syringe actuating mechanism 107.

Figure 8:
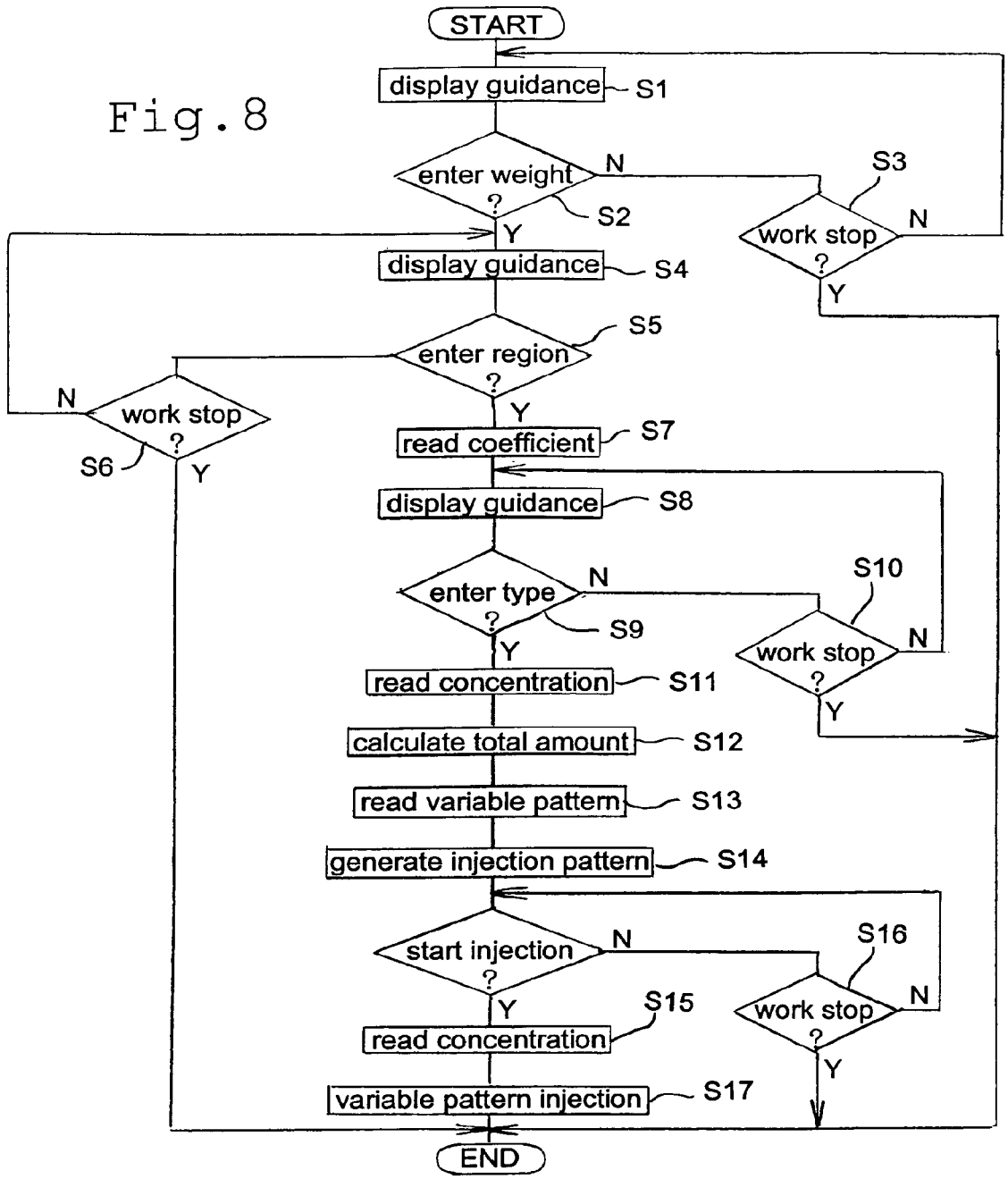
FIG. 8 a flowchart of a processing sequence of the liquid injector.
Figure 9:
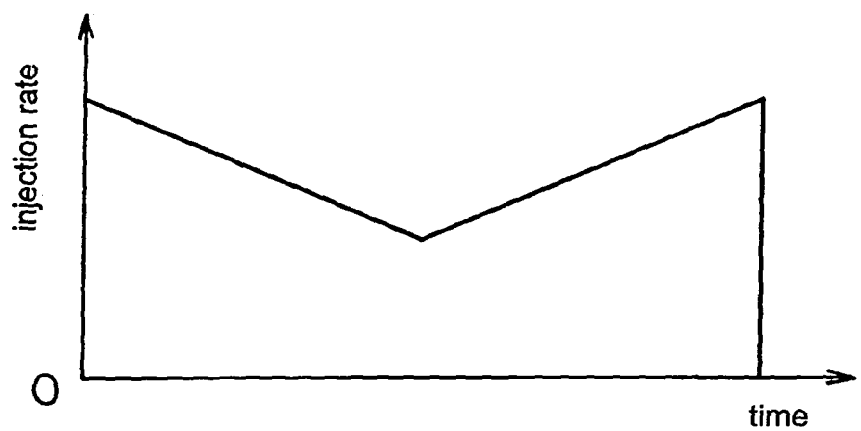
FIG. 9 is a diagram showing a variable pattern of an injection rate according to a modification.

Then, the operator makes an input action on console panel 104 to instruct liquid injector 100 to start operating. As shown in FIG. 8, liquid crystal display panel 109 displays a guidance message "ENTER NUMERICAL VALUE OF SUBJECT'S BODY WEIGHT IN KILOGRAMS. IF DEFAULT VALUE IS USED, ENTER 00, AND IF PREVIOUS NUMERICAL VALUE IS USED, ENTER 01." in step S1.

The operator then enters the numerical value of the body weight of the subject on console panel 108 in step S2. The entered numerical value of the body weight of the subject is stored in a working area of RAM 113. If "00" is entered, then a default value registered as an average body weight value is copied from ROM 112 to RAM 113. If "01" is entered, then the previous numerical value stored in RAM 113 is made effective.

Thereafter, liquid crystal display panel 109 displays a guidance message "ENTER REGION TO BE IMAGED WITH FOLLOWING NUMBER. HEAD=1, CHEST=2, ABDOMEN=1, LEG=4, ARM=2" in step S4. The operator enters a number representing a region to be imaged on console panel 108 in step S5. Based on the entered number, CPU 111 reads the data of a coefficient from a data file in ROM 112, and holds the data of the coefficient in RAM 113 in step S7.

Thereafter, liquid crystal display panel 109 displays a guidance message "ENTER TYPE OF CONTRAST MEDIUM TO BE USED WITH FOLLOWING NUMBER. xx CO. xx CONTRAST MEDIUM=1, . . . " in step S8. The operator then enters a number representing a type of contrast medium on console panel 108 in step S9. Based on the entered number, CPU 111 reads the data of a concentration of iodine contained in the contrast medium ROM 112, and holds the data of the concentration in RAM 113 in step S11.

CPU 111 performs a calculating process to calculate a total amount of contrast medium to be injected by multiplying the total amount of iodine contained in the contrast medium whose data is registered depending on the body weight of the subject, by body weight of the subject, dividing the multiplied amount by the concentration of contained iodine, and multiplying the divided amount by the coefficient assigned to the region to be imaged, in step S12.

Then, CPU 111 reads the data of the variable pattern from ROM 112 in step S13. CPU 111 generates the data of an injection pattern corresponding to the variable pattern for injecting the calculated total amount of contrast medium in a predetermined period of time in step S14. For example, if the variable pattern is set according to a predetermined waveform as shown in FIG. 6, then the waveform of the variable pattern is vertically moved with the injection time unchanged, so that the area surrounded by the waveform and the x- and y-axes will be commensurate with the total amount of contrast medium to be injected.

The operator then makes an input action on the console panel 108 to start injecting the contrast medium in step S15. The CPU 111 controls operation of syringe actuating mechanism 107 according to the injection pattern, thereby injecting the calculated total amount of contrast medium at the injection rate that varies with time according to the variable pattern, in the predetermined period of time in step S17.

Advantages of the Liquid Injector:

Since liquid injector 100 varies the injection rate of the contrast medium with time according to the variable pattern, a state in which the CT value approximates the optimum level can be maintained, allowing CT scanner 300 to capture an optimum fluoroscopic image of the subject. As the contrast medium is consumed in a minimum amount that is required, the contrast medium can be saved without excessive consumption, contributing to the health of the subject.

Figure 7:
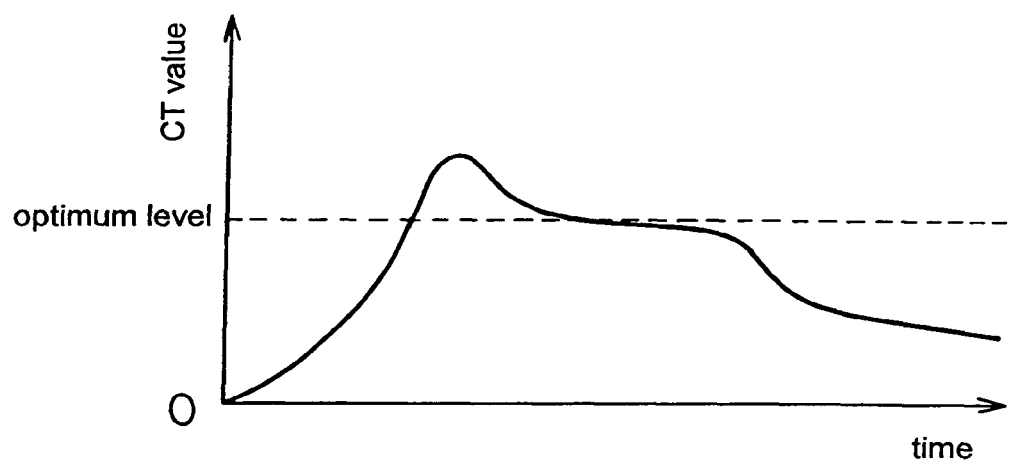
FIG. 7 is a diagram showing a CT value representing an image contract as it varies with time.

An experiment was conducted in which a contrast medium was injected into a subject according to a variable pattern such that the injection rate is linearly reduced for a certain period of time from the start of injection, and subsequently kept constant, as shown in FIG. 6. The results of the experiment has confirmed that a state in which the CT value approximates the optimum level as shown in FIG. 7 is maintained for a long period of time.

Furthermore, liquid injector 100 according to the present embodiment can automatically calculate a total amount of contrast medium to be injected into a subject for a predetermined period of time when the body weight of the subject, a region to be imaged of the subject, and a type of contrast medium to be used are entered into liquid injector 100. Consequently, the operator is not required to carry out complex calculations to determine a total amount of contrast medium to be injected into the subject. In particular, inasmuch as liquid injector 100 automatically generates an injection pattern depending on the calculated total amount of contrast medium to be injected and the variable pattern, the operator does not need to perform a complex process of varying the injection rate of the contrast medium with time.

Modifications:

The present invention is not limited to the above embodiment, but various changes and modifications may be made therein without departing from the scope of the invention. For example, as shown in FIG. 6, the variable pattern such that the injection rate is linearly reduced for a certain period of time from the start of injection, and subsequently kept constant is illustrated in the above embodiment. The variable pattern may be set to various data based on experimental results. For example, the injection rate may be varied nonlinearly.

Figure 10:
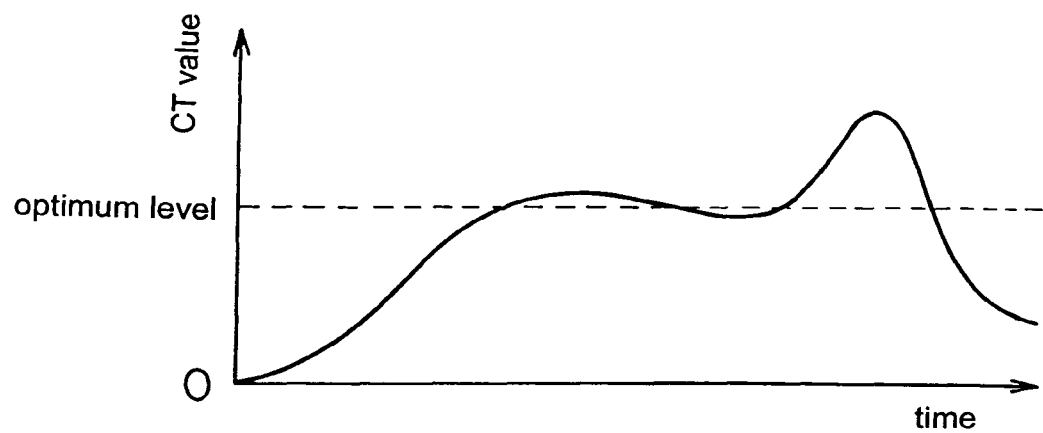
FIG. 10 is a diagram showing a CT value as it varies with time according to the modification.
Figure 11:
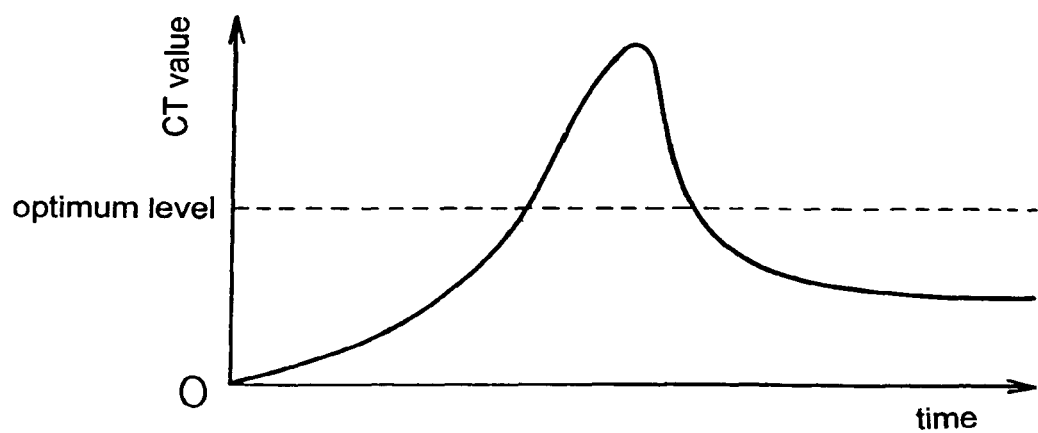
FIG. 11 is a diagram showing a CT value as it varies with time according to a conventional liquid injector.

The inventor of the present invention conducted an injection experiment with a variable pattern such that the injection rate is linearly reduced for a certain period of time from the start of injection, and subsequently linearly increased. It has been confirmed from the results of the injection experiment that a state in which the CT value approximates the optimum level as shown in FIG. 10 is maintained for a long period of time.

In the above embodiment, only the data of the body weight of a subject is entered as a parameter of the subject in order to calculate a total amount of contrast medium to be injected into the subject. However, various data of the height, gender, age, body shape, etc. of a subject may be used to calculate a total amount of contrast medium to be injected into the subject. While it has been illustrated in the above embodiment that the operator enters a numerical value of the body weight of a subject, it is possible for the operator to select one of body weight ranges, e.g., "less than 10 (Kg), 10-20 (Kg), . . . ".

In the above embodiment, the operator manually enters the data of the body weight of a subject on console panel 108. However, as disclosed in Japanese patent application No. 2002-393968 filed by the applicant of the present application, if a medical record of a subject is available in the form of electronic data, then the data of the body weight of the subject may be read from the medical record.

Since CT scanner 300 has a bed for supporting the subject thereon, the body weight of the subject may be measured using the bed and the data thereof may be entered into liquid injector 100. When the subject is to be imaged by CT scanner 300, the data of a region to be imaged of the subject is entered of necessity into CT scanner 300. Consequently, the entry of the data of a region to be imaged of the subject into CT scanner 300 and the entry of the data of a region to be imaged of liquid injector 100 may be performed in common.

In the above embodiment, the operator enters the data of the type of a contrast medium to be used on console panel 108. However, as disclosed in Japanese patent application No. 2002-021762 filed by the applicant of the present application, the type of syringe 200 mounted on injection head 101 may be detected to determine the type of a contrast medium to be used.

In the above embodiment, CT scanner 300 is used as an imaging diagnostic apparatus, and liquid injector 100 injects a contrast medium for use therewith into subjects. However, an MIR apparatus may be used as an imaging diagnostic apparatus, and liquid injector 100 may inject a contrast medium for use therewith into subjects.

While preferred embodiments of the present invention have been described using specific terms, such description is for illustrative purposes only, and it is to be understood that changes and variations may be made without departing from the spirit or scope of the following claims.

What is claimed is:
1. A liquid injector for injecting at least a contrast medium into a subject whose fluoroscopic image is to be captured by an imaging diagnostic apparatus, comprising:
   a liquid injection mechanism for injecting contrast medium into a subject; and
   a computer unit configured to:
   read out data of a base operation-condition, including (i) data of injection rate for contrast medium and (ii) data of a predetermined injection time for an injection;
   calculate a total volume of the contrast medium to be injected, based on data of a necessary dose of effective component per unit weight, a subject's weight, and a concentration of the effective component;
   make an injection pattern based on the base operation-condition and the calculated total volume of the contrast medium, by changing the injection rate of the base-operation condition depending on the total volume, with said predetermine injection time unchanged for all volumes of the contrast medium; and;
   control the injection mechanism to perform an injection in accordance with said injection pattern without changing any injection parameter during the injection.

2. The liquid injector of claim 1, further comprising:
   an injection head configured to hold at least one syringe, comprising the liquid injection mechanism; and
   a console electrically connected to the injection head comprising the computer unit.

3. The liquid injector of claim 2, wherein said console is further configured to receive one or more data selected from patient's weight data, a region to be imaged data, and contrast medium data.

4. The liquid injector of claim 3, wherein said console is further configured to receive a patient's weight data.

5. The liquid injector of claim 3, wherein said console is further configured to provide a graphical user interface for a user to select a classification of a patient's weight.

6. The liquid injector of claim 2, wherein said console further comprises a screen display.

7. The liquid injector of claim 1, wherein a pattern of said injection rate for the contrast medium is constant.

8. The liquid injector of claim 2, wherein said console further comprises a data storage device that stores data of a variable pattern, wherein said variable pattern includes a first phase in which an injection rate for contrast medium is linearly decreased.

9. The liquid injector of claim 8, wherein said variable pattern further comprises a second phase for contrast medium injection.

10. A medical imaging system, comprising:
an imaging apparatus for scanning a subject; and
the liquid injector according to claim 1.

11. The medical imaging system of claim 10, further comprising at least one electronic medical record.

12. The medical imaging system of claim 10, further comprising at least a syringe for a contrast medium.

13. A method for injecting a contrast medium into a subject using a liquid injector whose fluoroscopic image is to be captured by an imaging diagnostic apparatus or other data processing apparatus, comprising:
registering data of a base operation-condition, including (i) data of an injection rate and (ii) data of a predetermined injection time for an injection; and
controlling operation of said liquid injector, said imaging diagnostic apparatus or said other data processing apparatus so as to:
read out the base operation-condition;
calculate a total volume of the contrast medium to be injected, based on data of necessary dose of effective component per unit weight, data of subject's weight, and data of concentration of the effective component,
make an injection pattern based on the base operation-condition and the calculated total volume of the contrast medium, by changing the injection rate, depending on the total volume, with said predetermined injection time unchanged for all volumes of the contrast medium; and
perform an injection in accordance with said injection pattern, without changing any parameter during the injection.

14. The method of claim 13, further comprising inputting data of necessary dose of effective component per unit weight, data of subject's weight, and data of concentration of the effective component.

15. The method according to claim 13, further comprising:
registering data of different concentrations for each contract medium;
registering data of coefficients assigned to respective regions to be imaged of a patient;
accepting a selection of data relating to a patient's weight, a region to be imaged of patient, and contrast medium;
reading data of the concentration based on the contrast medium;
reading coefficient data based on the selected region to be imaged; and
correcting said total amount of the contrast medium to be injected, which has been increased or reduced in proportion to said body weight and in inverse proportion to said concentration, by multiplying said total amount by said one of the coefficients.

* * * * *